United States Patent [19]
Myers et al.

[11] Patent Number: 6,090,830
[45] Date of Patent: Jul. 18, 2000

[54] CONTROLLED RELEASE COMPOSITIONS AND METHODS FOR THE TREATMENT OF HYPERLIPIDEMIA

[75] Inventors: Michael Myers, Reston; Pradeepkumar P. Sanghvi, Herndon, both of Va.

[73] Assignee: Fuisz International Ltd., Dublin, Ireland

[21] Appl. No.: 09/119,225

[22] Filed: Jul. 20, 1998

[30] Foreign Application Priority Data

Oct. 7, 1997 [IE] Ireland ...................................... 970731

[51] Int. Cl.[7] .......................... A61K 31/44; A61K 31/40; A61K 31/35; A61K 31/21
[52] U.S. Cl. ............................................................. 514/356
[58] Field of Search ...................................... 514/356, 419, 514/451, 460, 510, 824, 964

[56] References Cited

U.S. PATENT DOCUMENTS

| | | | |
|---|---|---|---|
| H1286 | 2/1994 | Eisman et al. | 514/91 |
| 5,157,025 | 10/1992 | Aberg et al. | 514/80 |
| 5,260,305 | 11/1993 | Dennick | 514/255 |
| 5,445,769 | 8/1995 | Rutkowski et al. | 264/8 |
| 5,458,823 | 10/1995 | Perkins et al. | 264/8 |
| 5,683,720 | 11/1997 | Myers et al. | 424/489 |

*Primary Examiner*—Kimberly Jordan
*Attorney, Agent, or Firm*—Sandra M. Nolan; Richard D. Schmidt

[57] ABSTRACT

Lipid lowering dosage units, to be used once a day, produce minimal side effects. They contain a combination of microspheres formulated to co-deliver a HMG-CoA reductase inhibitor component and a niacin component.

11 Claims, No Drawings

CONTROLLED RELEASE COMPOSITIONS AND METHODS FOR THE TREATMENT OF HYPERLIPIDEMIA

FIELD OF THE INVENTION

This invention relates to lipid lowering agents, and more particularly, to an improved dosage unit of HMG-CoA reductase inhibitor and niacin having diminished side effects. A method of using the novel dosage unit of the invention in treating hyperlipidemia is also provided.

BACKGROUND OF THE INVENTION

Combinations of HMG CoA reductase inhibitors, the so-called "statins," and other types of lipid regulating agents are known in the art in the treatment of Low Density Lipoprotein (LDL) Cholesterol. Unfortunately, one or more of these agents suffer from various drawbacks. At least some members of the reductase inhibitor family, in particular lovastatin, are very poorly soluble in water. This results in low bioavailability to the patient. Other agents, such as niacin (nicotinic acid), have much higher solubilities, but can be toxic to the patient or produce discomforting symptoms. Liver damage is thus a concern when treating for hyperlipidemia with niacin. In addition, niacin can produce gastrointestinal problems when taken in an immediate release composition administered several times daily. "Flushing" is another common occurrence in which painful swelling in the joints and elsewhere occurs for some minutes after ingestion.

U.S. Statutory Invention registration H1286, published Feb. 1, 1994, discusses various combinations of HMG CoA reductase inhibitors with agents which lower lipids via other mechanisms. Niacin, or nicotinic acid, is among the agents discussed.

U.S. Pat. No. 5,260,305 shows combinations of pravastatin and nicotinic acid and methods for lowering serum cholesterol levels with such combinations. The use of between 75 and 2,000 mg of nicotinic acid is disclosed.

U.S. Pat. No. 5,157,025 relates to methods for lowering serum cholesterol which employ phosphorous-containing ACE inhibitors in combination with other cholesterol lowering agents. Nicotinic acid is recited at column 20, line 61.

While combinations of lipid lowering agents are known, there is still a need for combinations in which each of the types of active components therein have been specifically formulated in order to optimize their release properties and, thereby, significantly minimize the likelihood that they will produce unwanted side effects when consumed. At the same time, there is a need for a dosage regimen which is more convenient to the patient than those currently available in the art. This invention addresses that need.

SUMMARY OF THE INVENTION

An oral dosage unit of lipid lowering agents for once a day use is made up of:
  (A) immediate release microspheres containing less than about 40 mg of at least one HMG CoA reductase inhibitor; and
  (B) sustained release microspheres containing less than about 2000 mg of niacin. Further, a pharmaceutical product for oral administration in unit dosage form for treating hyperlipidemia comprises an immediate release HMG-CoA reductase inhibitor component and a sustained release niacin component.

A method of using a combination of lipid lowering agents comprises orally administering to a subject a dosage unit containing:
  (A) an immediate release HMG-CoA reductase inhibitor component; and
  (B) a sustained release niacin component.

In both the product and the method of the invention, the release characteristics of both the HMG-CoA reductase inhibitor and niacin components are optimized, providing minimal toxicity and other side effects to the patient.

DETAILED DESCRIPTION OF THE PREFERRED EMBODIMENTS

It has been previously established that both HMG-CoA reductase inhibitors and nicotinic acid derivatives, in particular niacin, are efficacious medicines for the treatment of hyperlipidemia through their effect of lowering the levels of Low Density Lipoprotein (LDL) Cholesterol. A combination unit of the two classes of drugs is now proposed with a single, daily dosing requirement with minimal, even barely detectable side effects. In this way, a much improved patient compliance record can be established as such incidences as liver damage, flushing or gastrointestinal discomfort, as well as other symptoms, are reduced to a minimum. The new drug dosage unit is thus a considerable advancement over either drug alone, as well as over any presently known combinations of the two classes of drugs. As hereinafter described, the release characteristics of both classes of drugs may be modified to provide release patterns which allow for the adaptation of the combination into a once daily single unit dosage.

A method of using the novel formulation of the invention comprises administering a dosage unit having an immediate release HMG-CoA reductase inhibitor component together with a sustained release niacin component. In this way, the lowering of lipid levels in individuals in need of such treatment can be achieved. "Immediate release," as used herein, refers to the fact that no extrinsic factors delay the in vitro release of the drug. "Sustained release," on the other hand, is defined as a prolonged release pattern, often achieved through the use of excipients or coatings, hereinafter described. In this way, the drug is released more evenly, usually over a longer period of time.

It may also be preferred in the sustained release niacin component composition that $T_{max}$ occur later than would be the case with the same drug in an immediate release formulation. In the same way, it may also be desirable to shorten the time to $T_{max}$ for the immediate release HMG-CoA reductase inhibitor component than is usually possible. The two $T_{max}$'s may thus approach one another, or even coincide. By doing so, the side effects associated with the use of the two classes of drugs may be reduced significantly. ($T_{max}$, as those skilled in the art will recognize, is the time after dosage for maximum plasma concentration of the drug).

As that term is used herein, HMG-CoA refers to the enzyme 3-hydroxy-3-methylglutaryl coenzyme A. Examples of HMG-CoA reductase inhibitors include the family of statins. Examples of statins include fluvastatin sodium, pravastatin sodium, simvastatin, and lovastatin, as well as any others which may be known in the art (including all pharmaceutically acceptable salts of any of the foregoing). Any of the foregoing, either alone or in combination, can function as the HMG-CoA reductase inhibitor component of the combination drug of the invention. Of these, lovastatin is preferred.

Niacin shall refer to nicotinic acid, a B complex vitamin, and all derivatives thereof in whatever form as is known in the art (including all pharmaceutically acceptable salts of any of the foregoing). Of these, niacin, either alone or in combination with other nicotinic acid derivatives, can function as the niacin component of the combination drug of the invention. Niacin itself is particularly preferred.

As heretofore discussed, HMG-CoA reductase inhibitors are in some cases very poorly soluble drugs with low oral bioavailability. Of these, lovastatin can present a particular problem. The challenge associated with this class of drug substances is therefore to enhance intrinsic solubility, thereby improving oral bioavailability. A solubilizing agent, and more preferably, a surfactant, is desirably utilized as part of the HMG-CoA reductase inhibitor component to enhance the solubility characteristics of the HMG-CoA reductase inhibitor. Those surfactants which are overall hydrophilic in nature, and especially ethylene oxide-propylene oxide copolymer surfactants (sometimes referred to as "poloxamers") are especially preferred. Those poloxamers having an ethylene oxide content within the range of about 60 to 90%, more desirably about 70 to 80%, are especially preferred. One class of surfactants is marketed under the trademark PLURONIC, and is available from BASF Corporation of Wyandotte, Mich. Others are sold under the trade names LUTROL and MONOLAN. Of the class of PLURONIC surfactants, PLURONIC F 68 is especially preferred as a mechanism for enhancing the solubility of the HMG-CoA reductase inhibitor in the drug dosage unit of the invention. Other solubilizing agents include the polyethylene glycol and their derivatives, for example, GELUCIRE or GELUCIRE 50/13 (Gattefosse), which is a polyethylene glycol-32 glyceryl palmitostearate ester (HLB 13).

While other forms are highly contemplated, a highly preferred form of HMG-CoA reductase inhibitor and solubilizing agent is in microsphere form. Microspheres are tiny orbs preferably formed as a result of liquiflash processing of the HMG-CoA reductase inhibitor together with the solubilizing agent.

Liquiflash processing techniques, together with the apparatuses used in such processing, are described in the art. The apparatus described in U.S. Ser. No. 08/874,215, filed on Jun. 13, 1997, is one such apparatus. A spinner head which includes a base and a cover is aligned with and spaced from the base. The spinner head also includes a plurality of discrete elongate spaced apart heating elements positioned between the base and the cover and define a perimetrical configuration. The base, the cover and the heating elements mutually defining a chamber for accommodating therein a solid non-solubilized feedstock material capable of undergoing physical transformation with the application of heat and force. In addition, a flow restricting device is provided for restricting expulsion of the feedstock material from the chamber. The flow restricting device includes a plurality of plates, each plate being removably insertable in a space between the heating elements. The restricting device further includes an elongate generally annular housing having an inside and outside diameter and having a plurality of circumferentially spaced passages extending therethrough. The housing is positionable over the heating elements with the tubular heating elements residing within the passages. The annular housing defines longitudinal radially-directed slots between the passages so as to permit passage of the feedstock material therethrough. One of the restricting plates is insertable in each of the slots and engageable with the feedstock material as it is expelled. In one embodiment, the restricting plate is a substantially elongate plate having a pair of opposed sides including a plurality of radially extending grooves. The grooves forming a pathway for the expelled feedstock material. The grooves extend generally perpendicular to the elongate plate and extend radially outwardly from the spinner head. The grooves are substantially V-shaped in cross-section and have a varying width, the width decreases as the groove extends radially outward. In addition, the plate has a beveled inside edge facing a central chamber in order to assist in channeling feedstock through the grooves. The plate may include a tab extending upwardly from a top portion, in order to provide a gripping area for facilitating removal of the plate from the spinner head. The plate is secured to the spinner head by a latch member extending substantially orthogonally outwardly from at least one side of the plate and is engageable with the annular processing wall. Upon rotation of the spinner head, the plate is urged radially outwardly by centrifugal force and the latch member is urged against the annular processing wall, thereby preventing the plate from being expelled from the slot.

The liquiflash process is also described in U.S. Ser. No. 08/330,412, filed on Oct. 28, 1994 (corresponding to published EP 709086 A3), and will issue as a U.S. patent on Nov. 7, 1997. In addition, U.S. Pat. Nos. 5,445,769 and 5,458,823 show devices useful in the production of liquiflash microspheres. All of the foregoing patent references are incorporated herein by reference.

Microspheres containing HMG-CoA reductase inhibitor and solubilizing agent are made from binary feedstocks which are spheronized using liquiflash techniques. The feedstocks contain from about 5 to 80% of the aforesaid reductase inhibitor, together with about 95 to 20% of the solubilizing agent. (Unless otherwise stated, all percentages recited herein are weight percentages based on total composition weight). Combinations containing about 5 to 40% reductase inhibitor and 95 to 60% solubilizer are even more preferred. Combinations containing about 20 to 40% reductase inhibitor together with about 80 to 60% solubilizer are also highly effective. It is also very highly desirable that the microspheres contain only the HMG-CoA reductase inhibitor and the solubilizing agent. Such a combination is highly effective, without the need for additional excipients in the microsphere.

Liquiflash processing (to make the microspheres) involves first providing the HMG-CoA reductase inhibitor and the solubilizing agent at a fairly small particle size, preferably on the order of about 1 millimeter or smaller. Milling and/or grinding may be undertaken by the skilled artisan as a preliminary step. The particles are then blended and used as a binary feedstock in a suitable device (heretofore described) wherein heat and pressure conditions are controlled to effect morphological changes in the feedstock. (For reductase inhibitors, temperatures on the order of about 60–90 degrees C, and rotational settings of about 50–70 Hz are generally preferred). Inside the device, the feedstock particles lose their resistance to liquid flow, and thereby become "liquiform." In this state, the feedstock material is physically transformed from its original solid state, through a liquid state and back to a solid state instantaneously. While the particles undergo this transformation, they are acted upon by centrifugal force, or another shearing force, which force separates them into discrete spherical particles. This may be termed spheronization. The particles exit the device as discrete microspheres on the order of about 10 to 600 microns in diameter, and generally within the range of about 50 to 300 microns in diameter. The aforesaid U.S. Pat. Nos. 5,445,769 and 5,458,823, and U.S. application Ser. Nos. 08/330,412 (EP 709 086 A3) and 08/874,215 set out fully the details of the liquiflash spheronization, microsphere formation processes. These disclosures are incorporated herein by reference.

A particularly preferred binary feedstock loading ratio of HMG-CoA reductase inhibitor to solubilizing agent is on the order of about 40:60. In other words, it is especially desirable that the HMG-CoA reductase inhibitor component of the dosage unit of the invention contain about 40% HMG-CoA reductase inhibitor and about 60% solubilizing agent.

A preferred oral dosage form of the invention will contain from about 0.1 to 100 mg HMG-CoA reductase inhibitor, more preferably from about 10 to 80 mg reductase inhibitor, and even more desirably about 10 to 40 mg reductase inhibitor. Any amount of the reductase inhibitor less than about 40 mg is often especially desirable. Lovastatin is the preferred inhibitor in any of the foregoing quantity ranges. Both the particular reductase inhibitor and the quantity chosen should be consistent with the invention's overall goal of providing a single, daily dose of the combination of HMG-CoA reductase inhibitor component and niacin component. In doing so, the goal of significantly reducing the noxious side effects associated with HMG-CoA reductase inhibitors and niacin should be a priority. While the single dosage unit is most highly preferred, any regimen or dosage unit which maximizes convenience to the patient over and above those dosage regimens presently available, are also contemplated herein.

The second major component of the drug dosage unit of the invention is a niacin component. Niacin is a relatively water-soluble drug and is typically dosed 3 or 4 times a day in an immediate release formulation. As a sustained release component in a once daily dosage unit, niacin exhibits significantly reduced side effects. This is because $T_{max}$ is delayed, and because a more even distribution of the niacin over time is effected as well.

While other forms are contemplated, the niacin component is preferably liquiflash processed in the same manner as heretofore described for the HMG-CoA reductase inhibitor component. In this way, niacin, either alone or together with a processing aid is subjected to liquiflash conditions. The niacin/processing aid feedstock component is then converted to discrete microspheres having the sizes heretofore set forth. Generally, the niacin component microspheres are typically made at temperatures of about 130–240 degrees C, and at a rotational speed of about 1800–4800 rpm. Niacin and/or niacin/processing aid liquiflash processed as heretofore described yields monodispersed microspheres which exhibit very few fines on the sphere surfaces.

The processing aid useful in forming the niacin component of the invention is desirably one or more compounds which will permit the niacin to be released more evenly over time, and will also delay $T_{max}$ of the niacin as compared to an immediate release formulation. It is highly desirable that the niacin component microspheres contain only the niacin and the processing aid.

The processing aid useful in forming the niacin component of the invention may be selected from wax materials. Of these, carnauba wax, White wax and combinations thereof preferred. Carnauba wax is especially desirable. Other processing aids include polymeric material. This polymeric material can be one or more compounds selected from the group consisting of polyvinylpyrrolidone (PVP), as well as cetyl alcohol, stearic acid and Comprotol 888 ATO, either alone or in combination with one or more of the aforesaid wax materials. Those skilled in the art may conceive of other materials which are useful as processing aids.

The niacin component feedstock (for liquiflash processing) preferably contains from about 95 to 5% of the aforesaid niacin, together with about 5 to 95% of the processing aid, with ratios of niacin/processing aid on the order of about 95:5 to 80:20 being particularly preferred. In an alternative embodiment, the niacin component may be 100% niacin, or other percentages.

Niacin is present in the combination and preferably present in the form of liquiflash produced microspheres in amounts of from about 10 to 2000 mg. Preferably, about 1000 mg. or less of niacin is utilized. In certain embodiments, it is desirable to utilize about 750 mg. or less, or even about 500 mg. or less of niacin.

To achieve sustained release effect, the niacin component microspheres are preferably further coated with one or more polymers, preferably a blend of polymers, at least two of which have different levels of hydrophilicity. Generally, one polymer is more hydrophilic than the other. More hydrophilic polymer coatings generally produce dosage forms which dissolve faster. Conversely, less hydrophilic polymers give coatings which dissolve relatively slowly. Applicants believe that the combination of polymers with different hydrophilicities produces coatings which dissolve in a sustained fashion, i.e., over a longer period of time.

Preferably, the more hydrophilic polymer is PVP, hydroxypropylcellulose polymer, or a similar polymer. PVPK-30, manufactured by BASF Corporation, and Klucel EF, manufactured by Aqualon, are suitable. Mixtures of the foregoing are also within the scope of the invention.

The less hydrophilic polymer component is typically a cellulosic polymer. Useful cellulosic polymer ingredients include one or more polymers selected from ethyl cellulose, polymethyl(meth)acrylate and the like, as well as mixtures thereof. In this regard, Ethocel (E-45) available from Dow Corporation is desirable.

The blend of polymers will typically be one in which the ratio of the less-hydrophilic polymer to the more hydrophilic polymer is from about 90:10 to about 50:50. Using ethyl cellulose (EC) polymer and PVP as examples, a suitable EC:PVP ratio will about 60:40 to about 50:50, with about 60:40 being highly effective.

The coating is applied to the microsphere substrates at a level of about 5 to 45% by weight of the niacin component, with coating levels on the order of about 10 to 25 weight percent being typical. Those skilled in the art may of course vary the aforesaid percentages according to their particular needs. Coating is generally effected using apparatus known in the art, for example, a fluidized bed, using known techniques such as the Wurster coating process. Coating generally takes place at about 20–30 degrees C.

While the use of multiple coatings is contemplated, the microspheres are generally coated once.

Solvents may be utilized in the coating process, and are generally selected from water, acetone, isopropyl alcohol and the like. About 0 to 20% of one or more plasticizers such as, for example, dibutyl sebacate, triethyl citrate and the like can also be used. Anti-tacking agents to prevent agglomeration of coated particles in amounts of about 0 to 50% are also within the scope of the invention. Typical anti-tacking agents include talc, colloidal, silica, magnesium stearate and the like.

An especially preferred niacin component would comprise about 85% niacin with about 15% carnauba wax as the processing aid. A preferred 60:40 combination of EC to PVP is then applied to the niacin component microspheres in amounts of about 10 to 15% by weight.

Once the coated niacin component microspheres are obtained, then these are combined with the heretofore described HMG-CoA reductase inhibitor component microspheres to yield the binary combination drug dosage unit of the invention. Suitable dosage units include capsules, caplets, tablets, suspensions, sachets and powders, as well as other forms known to those skilled in the art. Capsules and tablets are particularly preferred. The microspheres are combined into discrete dosage units using one or more diluents, fillers, binders, excipients, disintegrants, binders, glidants and lubricants, as well as any colorants and flavorants etc. which are available in the art. These may be chosen from such compounds as microcrystalline cellulose, crospovidone, Ac-Di-Sol, as well as others. The selection should be such that the chosen compounds facilitate the release of the herein described actives into the host.

By virtue of their discrete multiparticulate nature and the individual characteristics of the solubility enhanced HMG-CoA reductase inhibitor component microspheres and the sustained release niacin component microspheres, it is now possible to formulate a once-a-day dosage unit with greatly reduced side effects as compared with known hyperlipidemia agents available in the art today. Those skilled in the art may conceive of other physical forms of reductase inhibitor(s) and niacin that could be combined in a single unit daily dosage form with highly favorable side effect characteristics.

The following examples are provided by way of illustration of certain embodiments of the invention, and are not meant to be construed as limiting the scope thereof:

EXAMPLE 1

Lovastatin Microspheres

One kilogram of a 40:60 blend of lovastatin and PLURONIC F-68 surfactant was mixed together in a high shear mixer. The mix was spheronized using liquiflash processing in a spinner head at 60 Hz rotational speed at temperatures of 60–90 degrees C, to produce lovastatin microspheres having improved solubility.

Niacin Microspheres

One kilogram of an 85:15 blend of niacin and carnauba wax was mixed in a high shear mixer. The mix was spheronized using liquiflash processing in a spinner head at 50 Hz rotational speed at temperatures of 130–240 degrees C to produce niacin microspheres having improved $T_{max}$ properties.

Coating formulation: Ethylcellulose:Polyvinylpyrrolidone (60:40) was applied at 12.5% coating levels in a fluidized bed coater with a Wurster column (Glatt GPCG-1) to the niacin microspheres. The polymers were dissolved in acetone and sprayed on the microspheres at a rate of 12–16 g/min. maintaining product temperature at 23 degrees C.

Capsule Dosage Form

The improved microspheres equivalent to 20 mg. lovastatin and equivalent to 500 mg. niacin, respectively, could then be encapsulated in gelatin capsules.

EXAMPLE 2

The same procedure used in Example 1 could be used to produce a capsule dosage form with the equivalent to 10 mg. Of lovastatin and the equivalent to 750 mg. of niacin. Lovastatin:PLURONIC F68 surfactant ratio was 5:95. Niacin:carnauba wax ratio was 95:5. The coating level for the niacin microspheres was at 10% level with ethylcellulose:polyvinylpyrrilidone ratio of 70:30.

That heretofore described in the specification is by way of example only. Modifications to any of the embodiments listed herein are certainly within the scope of the invention, as it is set forth in the foregoing text and the accompanying claims.

We claim:

1. A pharmaceutical product for oral administration in unit dosage form for treating hyperlipidemia comprising:
    (A) an immediate release HMG-CoA reductase inhibitor component in microparticulate form; and
    (B) a sustained release niacin component in microparticulate form, wherein at least one of the microparticulates A and B is a controlled release microparticulate.
2. The product of claim 1 wherein (A) comprises a statin.
3. The product of claim 2 wherein said statin is at least one of: lovastatin, pravastatin, fluvastatin and simvastatin.
4. The product of claim 2 wherein (A) comprises lovastatin.
5. The product of claim 1 wherein (A) contains microspheres comprising lovastatin and a solubilizer and (B) contains microspheres comprising niacin or a niacin/processing aid combination, which microspheres have a sustained release coating thereon.
6. The product of claim 5 wherein the dosage unit is administered once a day.
7. The product of claim 5 or 6 wherein the dosage unit contains less than about 40 mg lovastatin and less than about 1000 mg niacin.
8. An oral dosage unit for once a day use comprising:
    (A) immediate release microspheres containing less than about 40 mg of at least one HMG CoA reductase inhibitor; and
    (B) sustained release microspheres containing less than about 1000 mg of niacin.
9. The dosage unit of claim 8 wherein the microspheres of (A) consist essentially of lovastatin and a solubilizer and the microspheres of (B) consist essentially of sustained release niacin microspheres coated with a sustained coating composition.
10. The dosage unit of claim 8 having reduced side effects.
11. The pharmaceutical product of claim 1 having reduced side effects.

* * * * *

UNITED STATES PATENT AND TRADEMARK OFFICE
Certificate

Patent No. 6,090,830                                           Patented: July 18, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael Myers, Reston, VA; Pradeepkumar Sanghvi, Herndon, VA; and Daniel M. Bell, Coral Gables, FL.

Signed and Sealed this Twenty-Ninth Day of July 2003.

SREENI PADMANABHAN
*Supervisory Patent Examiner*
Art Unit 1617